(12) United States Patent
Cho et al.

(10) Patent No.: US 9,220,794 B2
(45) Date of Patent: Dec. 29, 2015

(54) TWO-PHOTON FLUORESCENT PROBES FOR IMAGING OF TOTAL SULFIDE IN LIVE CELL AND TISSUE, AND QUANTITATIVE ESTIMATION OF TOTAL SULFIDE CONCENTRATION USING THE SAME

(71) Applicant: Korea University Research and Business Foundation, Seoul (KR)

(72) Inventors: Bong-Rae Cho, Seoul (KR); Chang Su Lim, Seoul (KR); Sajal Kumar Das, Seoul (KR); Sun Young Yang, Seoul (KR); Eun Sun Kim, Seoul (KR); Hoon Jai Chun, Seoul (KR)

(73) Assignee: KOREA UNIVERSITY RESEARCH AND BUSINESS FOUNDATION, Seoul (KR)

(*) Notice: Subject to any disclaimer, the term of this patent is extended or adjusted under 35 U.S.C. 154(b) by 0 days.

(21) Appl. No.: 14/459,944

(22) Filed: Aug. 14, 2014

(65) Prior Publication Data
US 2015/0118162 A1 Apr. 30, 2015

(30) Foreign Application Priority Data
Oct. 25, 2013 (KR) .................. 10-2013-0127504

(51) Int. Cl.
*A61K 49/00* (2006.01)
*C07D 277/66* (2006.01)

(52) U.S. Cl.
CPC .......... *A61K 49/0021* (2013.01); *C07D 277/66* (2013.01)

(58) Field of Classification Search
CPC .. C07C 247/16; C07D 277/66; C07D 263/57; A61K 49/0021
See application file for complete search history.

(56) References Cited

FOREIGN PATENT DOCUMENTS

KR 1020100000044 6/2010

OTHER PUBLICATIONS

Kim et al, Chem. Asian J., Two-Photon Fluorescent probes for Metal Ions, 2011, 6, pp. 58-69.*
Zaragoza Dorwald, Side Reactions in Organic Synthesis, 2005, Wiley-VCH Verlag GmbH & Co. KGaA, Weinheim, Preface. p. IX.*
Das et al, Chemical Communications, A Small Molecule Two-photon Probe for Hydrogen Sulfide in Live Tissues, 2012, 48, pp. 8395-8397.*
Lim et al, Analytical Chemistry, Quantitative Estimation of the Total Sulfide Concentration in Live Tissues by Two-Photon Microscopy, 2013, 85, pp. 9288-9295.*
Helmchen, F., et al., "Deep tissue two-photon microschopy," Nature Methods, 2005, vol. 2, No. 12, pp. 932-940.
Kim, H.M., et al., "Two-Photon Probes for Intracellular Free Metal Ions, Acidic Vesicles, and Lipid Rafts in Live Tissues," Accounts of Chemical Research, 2009, vol. 42, No. 7, pp. 863-872.
Zipfel, W.R., "Nonlinear magic: multiphoton microscopy in the biosciences," Nature Biotechnology, 2003, vol. 21, No. 11, pp. 1369-1377.

* cited by examiner

*Primary Examiner* — Paul A Zucker
(74) *Attorney, Agent, or Firm* — Duane Morris LLP; J. Rodman Steele, Jr.

(57) ABSTRACT

The present disclosure relates to a two-photon fluorescent dye for imaging total sulfide in vivo and a method for quantitatively estimating total sulfide concentration in vivo using the same. The two-photon fluorescent dye, which includes a compound of [Chemical Formula 1], can detect hydrosulfide ion and image total sulfide and allows quantitative estimation of total sulfide concentration in vivo.

7 Claims, 6 Drawing Sheets

[Chemical Formula 2-1]   [Chemical Formula 2-2]

FIG. 6

[Chemical Formula 2-2]   [Chemical Formula 2-3]

FIG. 7

[Chemical Formula 2-3]   [Chemical Formula 2-4]

FIG. 8

[Chemical Formula 2-4]  →  [Chemical Formula 2-5]

FIG. 9

[Chemical Formula 2-5]  →  [Chemical Formula 2-6]

FIG. 10

TWO-PHOTON FLUORESCENT PROBES FOR IMAGING OF TOTAL SULFIDE IN LIVE CELL AND TISSUE, AND QUANTITATIVE ESTIMATION OF TOTAL SULFIDE CONCENTRATION USING THE SAME

CROSS-REFERENCE TO RELATED APPLICATIONS

This application claims priority under 35 U.S.C. §119 to Korean Patent Application No. 10-2013-0127504 filed on Oct. 25, 2013 in the Korean Intellectual Property Office, the disclosure of which is incorporated herein by reference in its entirety.

TECHNICAL FIELD

The present disclosure relates to a two-photon fluorescent dye for imaging total sulfide in vivo, which is capable of detecting hydrosulfide ion and imaging total sulfide in vivo, and a method for quantitatively estimating total sulfide concentration in vivo using the same.

BACKGROUND

Hydrogen sulfide ($H_2S$) is a newly identified modulator. It is synthesized in mammalian tissues from cysteine and homocysteine by the enzymes cystathionine β-synthase (CBS) and cystathionine γ-lyase (CSE).

Hydrogen sulfide ($H_2S$) protects the gastric mucosa from injury, reduces inflammation of mucous membranes and enhances tissue repair. Dysfunction of hydrogen sulfide ($H_2S$) homeostasis is associated with ulcerative colitis, hypertension, atherosclerosis, cardiomyopathy, diabetic vascular disorders and diabetic nephropathy.

Current methods for detecting hydrogen sulfide ($H_2S$) in living cells or tissues include gas chromatographic, electrochemical and colorimetric methods. However, these methods require processing and/or breakdown of tissue and cell lysates. At present, no method capable of detecting hydrogen sulfide ($H_2S$) without damaging cells or tissues is available.

Although fluorescence imaging using a one-photon fluorescent dye is known as a method for detecting cells nondestructively, the one-photon fluorescent dye has to be excited with monochromatic light (~350-550 nm). Accordingly, there arise problems such as low penetration depth, photobleaching and cellular autofluorescence. In order to overcome these problems, two-photon microscopy (TPM) uses a two-photon probe capable of detecting the target substance deep in the living cells and tissues.

Two-photon microscopy is a new technique that allows imaging of living tissue up to a very high depth for a long period of time using two photons of low energy (Helmchen, F.; Denk, W. *Nat. Methods* 2005, 2, 932; Zipfel, W. R.; Williams, R. M.; Webb, W. W. *Nat. Biotechnol.* 2003, 2, 1369; Kim, H. M.; Cho, B. R. *Acc. Chem. Res.* 2009, 42, 863; Kim, H. M.; Cho, B. R. *Chem. Asian J.* 2011, 6, 58).

Korean Patent Publication No. 2010-0000044 discloses a two-photon dye for imaging acidic vesicles in vivo and a method for imaging acidic vesicles using the same. The two-photon dye selectively binds to acidic vesicles present in the cytoplasm and emits two-photon excited fluorescence.

Although a method for imaging acidic vesicles in vivo using a two-photon fluorescent dye has been presented as described above, there is no report about detection of hydrogen sulfide ($H_2S$).

Accordingly, development of a ratiometric two-photon fluorescent dye capable of detecting hydrosulfide ion and total sulfide in vivo without damaging cells or tissues is needed.

SUMMARY

The present disclosure is directed to providing a two-photon fluorescent dye for imaging total sulfide in vivo, which is capable of detecting hydrosulfide ion and imaging total sulfide in vivo.

The present disclosure is also directed to providing a method for quantitatively estimating total sulfide concentration in vivo using the two-photon fluorescent dye.

In a general aspect, the present disclosure provides a two-photon fluorescent dye for imaging total sulfide ($[H_2S]+[HS^-]$) in vivo, including a compound of [Chemical Formula 1]:

[Chemical Formula 1]

wherein $R_1$ is selected from a group consisting of a substituted or unsubstituted carbonyl group, a substituted or unsubstituted benzoxazole group and a substituted or unsubstituted benzothiazole group,

$R_2$ is an azide group or

$R_5$ is selected from a group consisting of deuterium, hydrogen, a substituted or unsubstituted $C_1$-$C_{30}$ alkyl group, a substituted or unsubstituted $C_6$-$C_{40}$ aryl group and a substituted or unsubstituted $C_2$-$C_{30}$ heteroaryl group, and $R_3$ and $R_4$ are selected from a group consisting of deuterium, hydrogen, a substituted or unsubstituted $C_1$-$C_{30}$ alkyl group and a hydrocarbon chain group containing at least one oxygen atom in a $C_1$-$C_{30}$ hydrocarbon chain.

Each of $R_1$ and $R_3$ through $R_5$ may be independently substituted with one or more selected from a group consisting of hydrogen, a cyano group,

-continued a halogen atom, hydroxyl group, a nitro group, a carboxyl group, a $C_1$-$C_{40}$ alkyl group, a $C_3$-$C_{40}$ cycloalkyl group, a $C_1$-$C_{40}$ alkoxy group, a $C_1$-$C_{40}$ alkylamino group, a $C_6$-$C_{40}$ arylamino group, a $C_3$-$C_{40}$ heteroarylamino group, a $C_1$-$C_{40}$ alkylsilyl group, a $C_6$-$C_{40}$ arylsilyl group, a $C_6$-$C_{40}$ aryl group, a $C_3$-$C_{40}$ aryloxy group and a $C_3$-$C_{40}$ heteroaryl group.

In an exemplary embodiment of the present disclosure, the compound represented by [Chemical Formula 1] may be selected from a group consisting of compounds represented by [Chemical Formula 2] through [Chemical Formula 9]:

[Chemical Formula 2]

[Chemical Formula 3]

[Chemical Formula 4]

[Chemical Formula 5]

[Chemical Formula 6]

[Chemical Formula 7]

[Chemical Formula 8]

[Chemical Formula 9]

wherein $R_3$ and $R_4$ are the same as defined in [Chemical Formula 1].

The two-photon fluorescent dye according to the present disclosure may be excited by a femtosecond pulse with a wavelength of 700-800 nm.

The two-photon fluorescent dye may detect hydrosulfide ion ($HS^-$) at a penetration depth of 100 μm or greater in vivo and may image total sulfide at a penetration depth of 100 μm or greater in vivo.

The two-photon fluorescent dye may have a two-photon action cross section ($\phi\delta_{max}$) of 10-30 GM at a wavelength of 740 nm.

The two-photon fluorescent dye may have a ratio of fluorescence intensities ($F_2/F_1$) measured at a short wavelength ($F_1$, ~350-550 nm) and a long wavelength ($F_2$, 560-780 nm) of 0.5-1.0.

In another general aspect, the present disclosure provides a method for quantitatively estimating total sulfide concentration in vivo using a reaction rate constant ($k_{obs}$), $k_2$ and a concentration ratio $[H_2S]/[HS^-]$ from a reaction of the compound of [Chemical Formula 1] with hydrosulfide ion ($HS^-$) in vivo.

The two-photon fluorescent dye for imaging total sulfide in vivo according to the present disclosure is excited by a femtosecond pulse with a wavelength of 700-800 nm and can image total sulfide ($[H_2S]+[HS^-]$) at a penetration depth of 100 μm. In addition, it exhibits good two-photon action cross section, high photostability and minimum interference from pH or cytotoxicity and can visualize total sulfide in living cells and tissues by two-photon microscopy (TPM) for a long period of time. In particular, the two-photon fluorescent dye of the present disclosure exhibits 110-fold increase in the fluorescence intensity ratio upon reaction with $HS^-$.

DETAILED DESCRIPTION OF EMBODIMENTS

The present disclosure relates to a two-photon fluorescent dye for imaging total sulfide in vivo, which is capable of detecting hydrosulfide ion and imaging total sulfide in vivo, and a method for quantitatively estimating total sulfide concentration in vivo using the same. Since the two-photon fluorescent dye according to the present disclosure is a ratiometric two-photon fluorescent dye for hydrosulfide ion, it can measure total sulfide concentration quantitatively.

Hereinafter, the present disclosure is described in detail.

The two-photon fluorescent dye of the present disclosure, which is represented by [Chemical Formula 1], selectively binds to hydrosulfide ion (HS⁻) deep in living cells and tissues and emits strong fluorescence.

[Chemical Formula 1]

In [Chemical Formula 1], $R_1$ is selected from a group consisting of a substituted or unsubstituted carbonyl group, a substituted or unsubstituted benzoxazole group and a substituted or unsubstituted benzothiazole group.

$R_2$ is an azide group or and $R_5$ is selected from a group consisting of deuterium, hydrogen, a substituted or unsubstituted $C_1$-$C_{30}$ alkyl group, a substituted or unsubstituted $C_6$-$C_{40}$ aryl group and a substituted or unsubstituted $C_2$-$C_{30}$ heteroaryl group, and

$R_3$ and $R_4$ are selected from a group consisting of deuterium, hydrogen, a substituted or unsubstituted $C_1$-$C_{30}$ alkyl group and a hydrocarbon chain group containing at least one oxygen atom in a $C_1$-$C_{30}$ hydrocarbon chain.

Each of $R_1$ and $R_3$ through $R_5$ may be independently substituted with one or more selected from a group consisting of hydrogen, a cyano group, a halogen atom, hydroxyl group, a nitro group, a carboxyl group, a $C_1$-$C_{40}$ alkyl group, a $C_3$-$C_{40}$ cycloalkyl group, a $C_1$-$C_{40}$ alkoxy group, a $C_1$-$C_{40}$ alkylamino group, a $C_6$-$C_{40}$ arylamino group, a $C_3$-$C_{40}$ heteroarylamino group, a $C_1$-$C_{40}$ alkylsilyl group, a $C_6$-$C_{40}$ arylsilyl group, a $C_6$-$C_{40}$ aryl group, a $C_3$-$C_{40}$ aryloxy group and a $C_3$-$C_{40}$ heteroaryl group.

Specifically, the compound represented by [Chemical Formula 1] may be selected from a group consisting of compounds represented by [Chemical Formula 2] through [Chemical Formula 9], although not being limited thereto.

[Chemical Formula 2]

-continued

[Chemical Formula 3]

[Chemical Formula 4]

[Chemical Formula 5]

[Chemical Formula 6]

[Chemical Formula 7]

[Chemical Formula 8]

[Chemical Formula 9]

In [Chemical Formula 2] through [Chemical Formula 9], $R_3$ and $R_4$ are the same as defined in [Chemical Formula 1].

The two-photon fluorescent dye according to the present disclosure may be excited by a femtosecond pulse with a wavelength of 700-800 nm.

The two-photon fluorescent dye according to the present disclosure selectively detects hydrosulfide ion (HS$^-$) at a penetration depth of 100 μm or greater, specifically 100-180 μm, in living cells or tissues. Upon reaction with the hydrosulfide ion (HS$^-$), a fluorescence intensity ratio ($F_2/F_1$) becomes 0.5-1.0. This corresponds to 110-fold increase as compared to before the reaction between the compound of [Chemical Formula 1] and the hydrosulfide ion (HS$^-$). In addition, since $H_2S$ is in equilibrium with HS$^-$, total sulfide concentration ([$H_2S$]+[HS$^-$] at a penetration depth of 100 μm or greater, specifically 100-180 μm, can be imaged in real time by two-photon microscopy (TPM) using the two-photon fluorescent dye. The quantitative distribution of the total sulfide can be estimated from two-photon microscopy (TPM) images.

The two-photon fluorescent dye may have a two-photon action cross section ($\phi\delta_{max}$) of 10-30 GM, specifically 10-15 GM, at a wavelength of 740 nm. Here, $\phi$ and $\delta_{max}$ are fluorescence quantum yield and maximum two-photon absorption cross section, respectively.

In another general aspect, the present disclosure provides a method for imaging total sulfide in vivo.

The method for imaging total sulfide in vivo includes: injecting the two-photon fluorescent dye into a cytoplasm; and observing two-photon excited fluorescence emitted from the two-photon fluorescent dye. The imaging of total sulfide in vivo is performed based on the change in two-photon excited fluorescence (TPEF).

The imaging method according to the present disclosure is advantageous in that accurate cell monitoring is possible since it allows imaging at a large depth and provides images with high fluorescence intensity from reaction with hydrosulfide ion (HS$^-$).

In another general aspect, the present disclosure provides a method for quantitatively estimating total sulfide concentration in vivo.

The total sulfide concentration in vivo can be quantitatively estimated using a kinetic method. Specifically, it is quantitated using a reaction rate constant ($k_{obs}$, $k_{obs}=k_2$[HS$^-$]) and $k_2$ and the ratio of [$H_2S$]/[HS$^-$].

The reaction rate constant ($k_{obs}$) is determined from the reaction of the compound of [Chemical Formula 1] with the hydrosulfide ion (HS$^-$) in vivo, $k_2$ is obtained as a slope of a curve of the reaction rate constant ($k_{obs}$) vs. [HS$^-$], and [$H_2S$]/[HS$^-$] is obtained from [$H_2S$]/[HS$^-$]=[H$^+$]/$K_a$.

More specifically, the rate equation for the reaction between the compound of [Chemical Formula 1] and the hydrosulfide ion (HS$^-$) in vivo may be expressed as follows.

$$-d[A]/dt = k_2[A][HS^-] \qquad (1)$$

wherein [A] is the concentration of the compound of [Chemical Formula 1] at time t.

The ratio [HS$^-$]/[$H_2S$] can be expressed as follows.

$$[HS^-]/[H_2S] = K_a/[H^+] \qquad (2)$$

Assuming [HS$^-$]≫[A], the rate equation can be expressed as follows.

$$-\ln[A]/[A]_0 = k_{obs}t \qquad (3)$$

wherein [A]$_0$ is the concentration of the compound of [Chemical Formula 1] at t=0 and $k_{obs}=k_2$[HS$^-$].

The equation (3) can be applied to living cells and tissues wherein $H_2S$ homeostasis is maintained. If [$H_2S$] is maintained constant during measurement, the ratio [HS$^-$]/[$H_2S$] and [HS$^-$] should be constant at a given pH. Under this condition, $k_{obs}=k_2$[HS$^-$] and the rate equation is the same as the equation (3).

Assuming that the concentration of the compound of [Chemical Formula 1] and a pass length are small enough such that the fluorescence intensity is proportional to [A], fluorescence intensities at a short wavelength and a long wavelength at the given time can be expressed as follows.

$$F^0_2 = S_{A2}[A]_0 \qquad (4)$$

$$F_1 = S_{A1}[A] + S_{B1}[B] \qquad (5)$$

$$F_2 = S_{A2}[A] + S_{B2}[B] = S_{A2}[A] + S_{B2}([A]_0 - [A]) \qquad (6)$$

$$F^\infty_2 = S_{B2}[A]_0 \qquad (7)$$

wherein the subscripts 1 and 2 refer to the short wavelength and the long wavelength, $F^\infty_2$, $F_1$ and $F_2$ are fluorescence intensities at t=∞ and t, [B] is the concentration of a product produced from the reaction between the compound of [Chemical Formula 1] and the hydrosulfide ion (HS$^-$) at time t, and $S_{A2}$, $S_{A1}$, $S_{B1}$ and $S_{B2}$ are proportionality coefficients of A and B at the given wavelength.

The yield [A]/[A]$_0$ is determined by the following equation.

$$[A]/[A]_0 = (F^\infty_2 - F_2)/(F^\infty_2 - F^0_2) \qquad (8)$$

$$-\ln(F^\infty_2 - F_2)/(F^\infty_2 - F^0_2) = k_{obs}t \qquad (9)$$

The equation (9) assumes that a plot of $-\ln(F^\infty_2 - F_2)$ vs. t will be linear with a slope $-k_{obs}$. However, because of degradation of a tissue sample, it is difficult to measure $F^\infty_2$ from the image several hours later.

Figure 2:
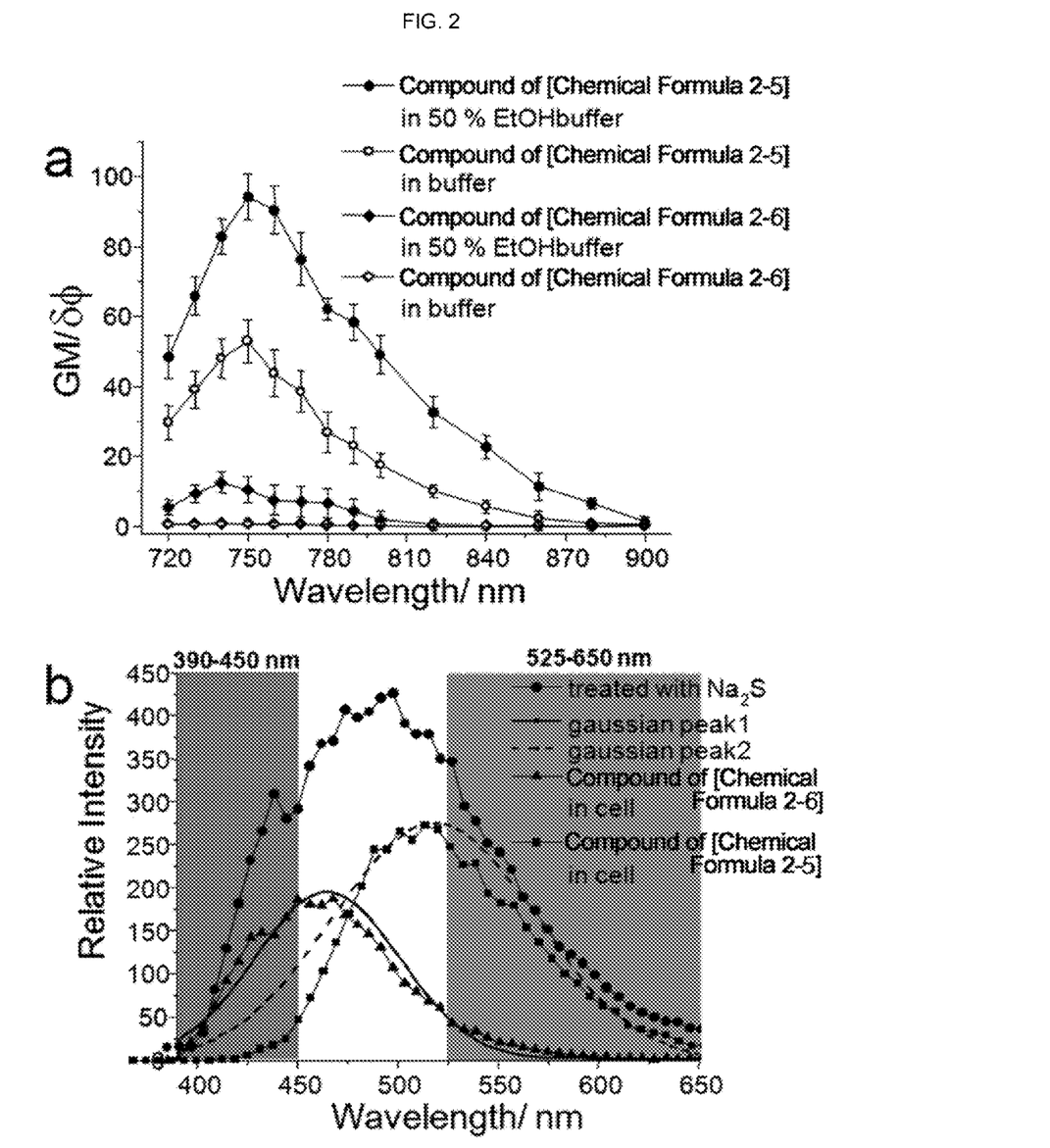
FIG. 2a shows two-photon action cross sections of a compound of [Chemical Formula 2-6] and a compound of [Chemical Formula 2-5] (3 μM) in HEPES buffer and HEPES/EtOH (1/1).
FIG. 2b shows two-photon excited fluorescence (TPEF) intensities of HeLa cells labeled with a compound of [Chemical Formula 2-6] or a compound of [Chemical Formula 2-5]. The broad curve (●) represents the TPEF spectrum of HeLa cells labeled with the compound of [Chemical Formula 2-6] after treatment with 100 μM $Na_2S$. The solid (-) and dotted (---) lines are the TPEF spectra of HeLa cells labeled with the compound of [Chemical Formula 2-6] (▲) and the compound of [Chemical Formula 2-5] (■) dissected into two Gaussian functions. Excitation wavelength was 750 nm.

Since $[A]_0=[A]+[B]$, $F^\infty_1$ can be ignored (FIG. 2b) and the fluorescence intensities of A and B are proportional to their concentration. Assuming $F^0_1=F^\infty_2$, $F^\infty_2$ can be expressed by the equation (10).

$$F^\infty_2 = F_1 + F_2 \quad (10)$$

However, because $F^0_1\{fourth\ root\}F^\infty_2$ in the real system, the equation (10) should be corrected as follows.

$$F^\infty_2 = (S_{B2}/S_{A1})F_1 + F_2 \quad (11)$$

$F^\infty_2$ can be measured based on the equation (11).

The equations (9) and (11) can be applied to two-photon (TP) processes using $F^{\infty TP}_2$, $F^{TP}_2$, $S_{B2}^{TP}$, $S_{A1}^{TP}$, $F^{TP}_1$ and $F^{TP}_2$ values. The superscript TP refers to the value measured in TP mode since one-photon and two-photon processes are essentially the same except for the excitation mode.

The $F^\infty_2$ values for the one-photon and two-photon processes calculated using the equation (11) were identical. Accordingly, it was confirmed that the kinetic method is useful.

Hereinafter, the present disclosure will be described in more detail through examples. However, the following examples are for illustrative purposes only and not intended to limit the scope of this disclosure. It will be obvious to those skilled in the art that various changes and modifications can be made thereto within the spirit and scope of the present disclosure set forth in the appended claims.

EXAMPLES

Synthesis Example 1

Synthesis of Two-Photon Fluorescent Dye Represented by [Chemical Formula 2-6]

1-1. Preparation of Compound Represented by [Chemical Formula 2-2]

Figure 5:
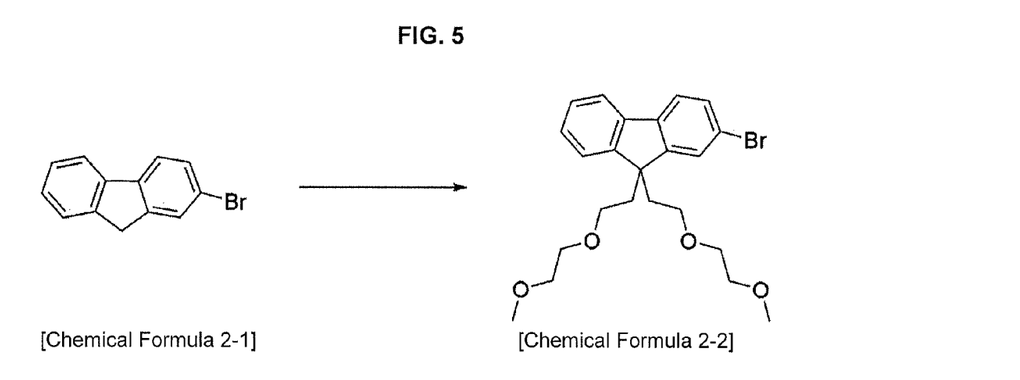
FIG. 5 shows a scheme used to prepare a compound of [Chemical Formula 2-2].

A compound of [Chemical Formula 2-2] was prepared according to [Scheme 1] as shown in FIG. 5.

10 g (40.8 mmol) of a compound of [Chemical Formula 2-1] and 25.7 g (93.8 mmol) of diethylene glycol monomethyl ether tosylate were dissolved in 150 mL of anhydrous DMSO and purged with dry nitrogen by repeated filling and deflating of a nitrogen balloon. To this was added freshly prepared 5.72 g (102 mmol) of anhydrous KOH powder. The resulting mixture was degassed and purged again with dry nitrogen. The mixture was stirred at 25° C. under nitrogen atmosphere for 12 hours and then poured into a beaker containing 300 mL of 1 N HCl. After adding 200 mL of diethyl ether, the mixture was stirred vigorously for 5 minutes. The organic layer was separated, washed with 100 mL of saturated $Na_2CO_3$ solution and 100 mL of brine, dried with $MgSO_4$, filtered and then concentrated. The concentrate was purified by column chromatography (30-50% ethyl acetate in n-hexane) to obtain 16.5 g (yield: 90.0%) of a compound represented by [Chemical Formula 2-2].

$^1$H NMR (400 MHz, $CDCl_3$): δ 7.65-7.63 (m, 1H), 7.57-7.52 (m, 2H), 7.46-7.39 (m, 2H), 7.33-7.31 (m, 2H), 3.29-3.15 (m, 14H), 2.78-2.74 (m, 4H), 2.41-2.37 (m, 4H);

$^{13}$C NMR (100 MHz, $CDCl_3$): δ 150.8, 148.2, 139.1, 139.0, 130.1, 127.5, 127.2, 126.3, 122.9, 120.9, 120.8, 119.6, 71.4, 69.6, 66.6, 58.7, 51.1, 39.2.

1-2. Preparation of Compound Represented by [Chemical Formula 2-3]

Figure 6:
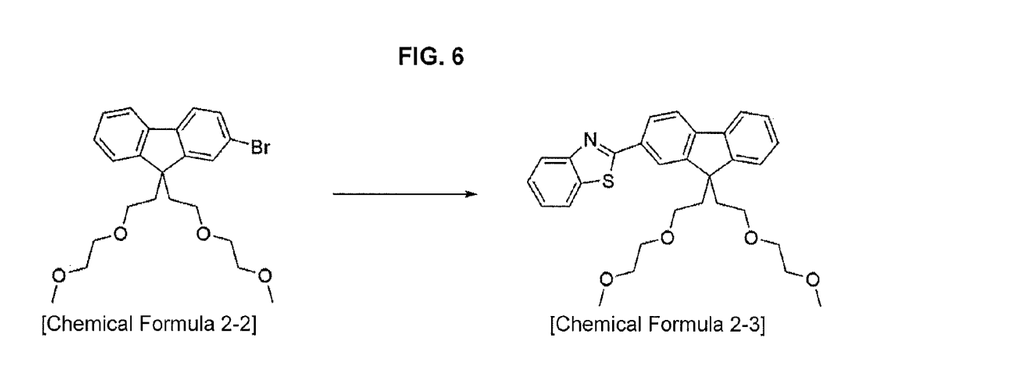
FIG. 6 shows a scheme used to prepare a compound of [Chemical Formula 2-3].

A compound of [Chemical Formula 2-3] was prepared according to [Scheme 2] as shown in FIG. 6.

15.0 g (33.4 mmol) of a compound of [Chemical Formula 2-2] and 5.50 mL (50.4 mmol) of benzothiazole were dissolved in 150 mL of anhydrous DMSO and purged with dry nitrogen by repeated filling and deflating of a nitrogen balloon. To this were successively added 16.5 g (50.6 mmol) of $Cs_2CO_3$, 1.12 g (5.0 mmol) of $Pd(OAc)_2$, 952 mg (5.0 mmol) of CuI and 15.0 mL of t-$Bu_3$P (10 wt % in hexane, 5.00 mmol). The resulting mixture was degassed and purged again with dry nitrogen. The mixture was vigorously stirred at 145° C. under nitrogen atmosphere for 12 hours, filtered and then washed with 300 mL of ethyl acetate. The filtrate was washed with 100 mL of 1 N HCl and 100 mL of brine, dried with $MgSO_4$ and filtered to obtain a black residue, which was dissolved again in 200 mL of ethyl acetate. After removing the solvent, the resulting crude product was purified by column chromatography (20-60% ethyl acetate in n-hexane) and recrystallized from ethyl acetate-hexane to obtain 14.5 g (yield: 86.0%) of a yellow solid compound represented by [Chemical Formula 2-3].

$^1$H NMR (300 MHz, $CDCl_3$): δ 8.19 (s, 1H), 8.10 (d, J=8.0 Hz, 2H), 7.93 (d, J=8.0 Hz, 1H), 7.79 (d, J=8.0 Hz, 1H), 7.75-7.73 (m, 1H), 7.53-7.37 (m, 5H), 3.29-3.17 (m, 14H), 2.85-2.75 (m, 4H), 2.59-2.44 (m, 4H);

$^{13}$C NMR (100 MHz, $CDCl_3$): δ 168.1, 154.1, 149.7, 149.5, 143.3, 139.4, 134.9, 132.5, 128.4, 127.4, 127.2, 126.3, 125.1, 123.3, 123.0, 122.0, 121.6, 120.3, 120.2, 71.6, 69.8, 66.9, 58.9, 51.4, 39.5;

HRMS (FAB) Calcd. for $C_{30}H_{34}NO_4S$ $[M+H]^+$: 504.2209. Found: 504.2209.

1-3. Preparation of Compound Represented by [Chemical Formula 2-4]

Figure 7:
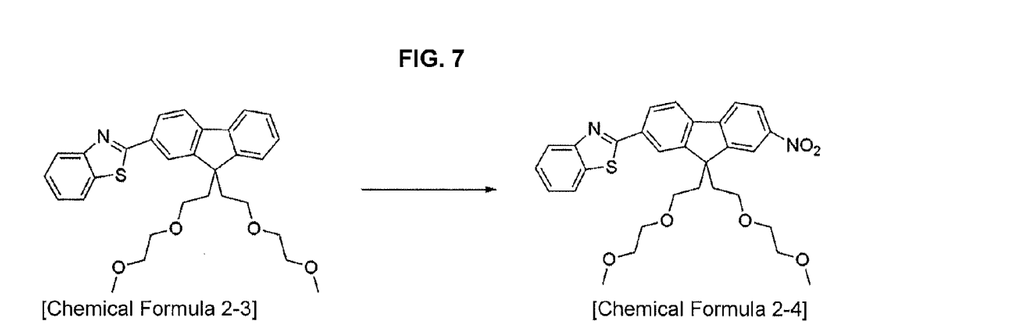
FIG. 7 shows a scheme used to prepare a compound of [Chemical Formula 2-4].

A compound of [Chemical Formula 2-4] was prepared according to [Scheme 3] as shown in FIG. 7.

10.0 g (19.9 mmol) of the compound of [Chemical Formula 2-3] was stirred in 50 mL of AcOH and 50 mL of $Ac_2O$. After adding 1.7 mL (39.7 mmol) of 93% $HNO_3$ dropwise at 25° C. for 10 minutes, the reaction was monitored (TLC) until the starting material was completely consumed (80-100 minutes or longer). The resulting mixture was poured into a beaker containing 200 mL of water. After adding 200 mL of ethyl acetate, the mixture was vigorously stirred for 5 minutes. The organic layer was separated, washed with 100 mL of water and 100 mL of brine, dried with $MgSO_4$ and then filtered. After removing the solvent, the resulting crude product was purified by column chromatography (20-50% ethyl acetate in n-hexane) and recrystallized from ethyl acetate-hexane to obtain 9.15 g (yield: 84.0%) of a yellow solid compound represented by [Chemical Formula 2-4].

M.p. −80-181° C. $^1$H NMR (400 MHz, $CDCl_3$): δ 8.38 (d, J=1.6 Hz, 1H), 8.30 (dd, J=1.6, 8.4 Hz, 1H), 8.27 (d, J=0.8 Hz, 1H), 8.15 (dd, J=0.8, 7.6 Hz, 1H), 8.11 (d, J=7.6, 1H), 7.94 (d, J=7.6, 1H), 7.89 (d, J=7.6, 1H), 7.85 (d, J=8.4, 1H), 7.52 (t, J=7.2 Hz, 1H), 7.41 (t, J=7.2 Hz, 1H), 3.27-3.12 (m, 14H), 2.98-2.81 (m, 4H), 2.59-2.56 (m, 4H);

$^{13}$C NMR (100 MHz, $CDCl_3$): δ 166.5, 153.4, 151.1, 150.7, 146.8, 145.0, 140.2, 134.4, 133.6, 125.9, 124.8, 122.6, 121.6, 121.1, 121.0, 119.8, 118.5, 70.9, 69.2, 66.2, 58.1, 51.7, 38.5.

1-4. Preparation of Compound Represented by [Chemical Formula 2-5]

Figure 8:
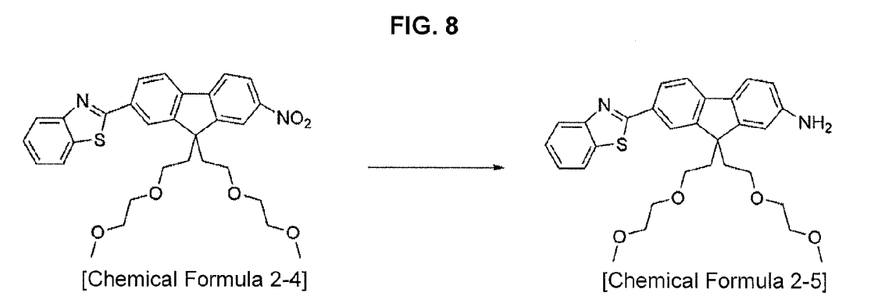
FIG. 8 shows a scheme used to prepare a compound of [Chemical Formula 2-5].

A compound of [Chemical Formula 2-5] was prepared according to [Scheme 4] as shown in FIG. 8.

9.00 g (16.4 mmol) of [Chemical Formula 2-4] and 2.63 g (49.20 mmol) of NH$_4$Cl were dissolved in 150 mL of EtOH and 50 mL of H$_2$O and refluxed under nitrogen atmosphere for 2 hours after adding 4.60 g (82.4 mmol) of Fe. After cooling to room temperature, the reaction mixture was filtered through celite and the residue was washed with 150 mL of ethyl acetate. The combined filtrate was concentrated to obtain a yellow residue which dissolved again in 200 mL of ethyl acetate and 100 mL of water. The organic layer was separated, washed with 100 mL of brine, dried with MgSO$_4$ and then filtered. After removing the solvent, the resulting crude product was purified by column chromatography (60-90% ethyl acetate in n-hexane) and recrystallized from ethyl acetate-hexane to obtain 7.65 g (yield: 90.0%) of a yellow solid compound represented by [Chemical Formula 2-5].

M.p. −134-135° C. $^1$H NMR (300 MHz, CDCl$_3$): δ 8.11 (d, J=1.2 Hz, 1H), 8.08-8.05 (m, 1H), 8.02 (dd, J=1.6, 7.8 Hz, 1H), 7.93-7.86 (m, 1H), 7.60 (d, J=7.8 Hz, 1H), 7.52-7.46 (m, 2H), 7.40-7.35 (m, 1H), 6.76 (d, J=2.1 Hz, 1H), 6.68 (dd, J=2.1, 8.4 Hz, 1H), 3.90 (s, br, 2H), 3.32-3.20 (m, 14H), 2.83-2.78 (m, 4H), 2.54-2.32 (m, 4H);

$^{13}$C NMR (100 MHz, CDCl$_3$): δ 168.2, 153.8, 151.3, 148.3, 147.3, 143.8, 134.5, 130.4, 129.6, 127.1, 125.9, 124.6, 122.5, 121.3, 121.25, 121.18, 118.4, 114.1, 109.1, 71.3, 69.5, 66.6, 58.6, 50.6, 39.5;

HRMS (FAB) Calcd. for C$_{30}$H$_{34}$N$_2$O$_4$S [M+H]$^+$: 519.2318. Found 519.2319.

1-5. Preparation of Compound Represented by [Chemical Formula 2-6]

Figure 9:
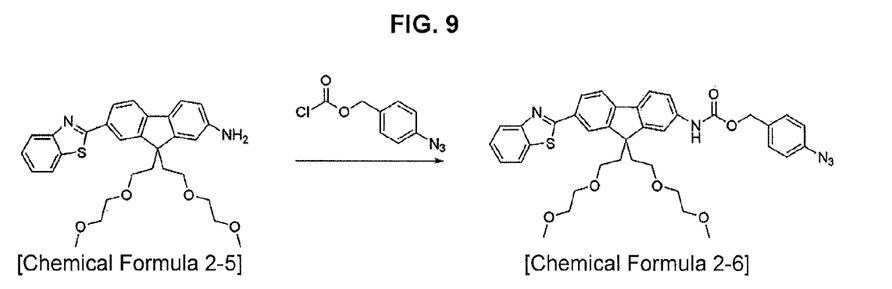
FIG. 9 shows a scheme used to prepare a compound of [Chemical 2-6].

A compound of [Chemical Formula 2-6] was prepared according to [Scheme 5] as shown in FIG. 9.

A mixture solution of trifluoroacetic acid (TFA, 0.50 g, 0.96 mmol) and anhydrous triethylamine (Et$_3$N, 0.28 mL, 2.0 mmol) in dried dichloromethane (CH$_2$Cl$_2$, 15 mL) was added dropwise to a solution of triphosgene (0.29 g, 0.98 mmol) in dried dichloromethane (CH$_2$Cl$_2$, 5 mL) under argon atmosphere at −10° C. After stirring at the same temperature for 3 hours, the stirred solution was slowly added dropwise to a solution of 4-azidobenzyl alcohol (0.23 g, 1.5 mmol) in dried dichloromethane (10 mL). After mixing 0.38 g of the resulting product with 0.52 g of the compound of [Chemical Formula 2-1] and stirring overnight at room temperature, the reaction was quenched with water (30 mL). After extraction with dichloromethane (3×50 mL), the organic layer was separated, washed with (30 mL) and then with brine (30 mL), dried with MgSO$_4$ and then filtered. After removing the solvent, the resulting crude product was purified by column chromatography (20-40% ethyl acetate in n-hexane) and filtered to a light yellow semisolid compound represented by [Chemical Formula 2-6] (0.346 g, yield: 52%).

$^1$H-NMR (400 MHz, CDCl$_3$): δ 8.15 (s, 1H), 8.07 (t, 2H, J=8.0 Hz), 7.92 (d, 1H, J=7.6 Hz), 7.70 (d, 1H, J=8.0 Hz), 7.66 (d, 1H, J=8.0 Hz), 7.52-7.37 (m, 5H), 7.09 (s, 1H), 7.04 (s, 2H), 5.19 (s, 2H), 3.30-3.17 (m, 14H), 2.84-2.77 (m, 4H), 2.54-2.41 (m, 4H);

$^{13}$C-NMR (100 MHz, CDCl$_3$): δ 168.2, 154.1, 153.1, 150.9, 149.5, 142.9, 140.1, 138.1, 134.83, 134.81, 132.7, 131.9, 129.9, 127.3, 126.3, 125.0, 122.9, 121.9, 121.5, 120.9, 119.7, 119.1, 71.6, 69.8, 66.8, 66.3, 58.8, 51.5, 39.5;

HRMS (FAB) Calcd. for C$_{38}$H$_{40}$N$_5$O$_6$S [M+H]$^+$: 694.2699. Found 694.2694.

The synthesized compound of [Chemical Formula 2-6] exhibits red-shift of maximum emission and increased two-photon action cross section.

Test Example 1

Photophysical Properties of Compound of [Chemical Formula 2-6]

In HEPES buffer (2-[4-(2-hydroxyethyl)piperazin-1-yl] ethanesulfonic acid; 20 mM HEPES, 100 mM KCl, pH 7.4), the compound of [Chemical Formula 2-6] and the compound of [Chemical Formula 2-5] showed maximum emission ($\lambda^{Fl}_{max}$) at 444 nm (φ=0.013) and 548 nm (φ=0.46) and maximum absorption ($\lambda_{max}$) at 360 nm (ε=2.50×10$^4$ M$^{-1}$cm$^{-1}$) and 363 nm (ε=3.91×10$^4$ M$^{-1}$cm$^{-1}$), respectively (Table 1).

Whereas the absorption ($\Delta\lambda_{max}$=8 nm) and emission ($\Delta\lambda^{Fl}_{max}$=31 nm) spectra of the compound of [Chemical Formula 2-6] was relatively less sensitive to solvent polarity, the emission spectrum of the compound of [Chemical Formula 2-5] showed large red-shift ($\Delta\lambda^{Fl}_{max}$=95 nm) in the order of 1,4-dioxane<DMF<EtOH<HEPES/EtOH (1/1)<HEPES buffer. The solvatochromic effect observed for the compound of [Chemical Formula 2-6] may have resulted from the small dipole moment.

In HeLa cells, the compound of [Chemical Formula 2-6] and the compound of [Chemical Formula 2-5] showed maximum emission at 450 nm and 520 nm, respectively, similarly to that measured in HEPES/EtOH (1/1) (Table 1). Accordingly, it can be seen that HEPES/EtOH (1/1) has polarity similar to that of the cellular environment.

TABLE 1

| | $\lambda^{(1)}_{max}$ [nm] (10$^{-4}$ ε)$^a$ | | $\lambda^{fl}_{max}$ [nm]$^a$ | | Φ$^b$ | | $\lambda^{(2)}$max [nm]$^c$ | | Φδ$_{max}^d$[GM]$^e$ | |
|---|---|---|---|---|---|---|---|---|---|---|
| | Chemical Formula 2-6 | Chemical Formula 2-5 | Chemical Formula 2-6 | Chemical Formula 2-5 | Chemical Formula 2-6 | Chemical Formula 2-5 | Chemical Formula 2-6 | Chemical Formula 2-5 | Chemical Formula 2-6 | Chemical Formula 2-5 |
| EtOH | 354 (4.27) | 381 (4.81) | 437 | 498 | 0.87 | 0.87 | | | | |
| HEPES/EtOH (1/1) | 352 (4.11) | 368 (4.77) | 440 | 530 | 0.41 | 0.81 | 740 | 750 | 12 | 94 |
| HEPES | 360 (2.50) | 363 (3.91) | 444 | 548 | 0.013 | 0.46 | 740 | 750 | 0.67 | 52 |
| Cell | — | — | 450 | 520 | — | — | — | — | — | — |

$^a$λ$_{max}$ of one-photon absorption and emission spectra.
$^b$fluorescence quantum yield.
$^c$λ$_{max}$ of two-photon absorption and emission spectra.
$^d$uncertainty in estimation, ±15%.
$^e$GM = 10$^{-50}$ cm$^4$s/photon.

Spectroscopic Measurements

Absorption spectra were recorded on the Hewlett-Packard 8453 diode array spectrophotometer and fluorescence spectra were obtained with the Amico-Bowman series 2 luminescence spectrometer with a 1-cm standard quartz cell. The spectral data obtained under various conditions are summarized in Table 1.

Test Example 2

Measurement of Ability of Detecting Sulfide

The ability of the compound of [Chemical Formula 2-6] of detecting HS⁻ in two-photon (TP) mode was measured.

In HEPES buffer, the two-photon action cross section ($\phi\delta$) of the compound of [Chemical Formula 2-6] was 1 GM at 740 nm, whereas that of the compound of [Chemical Formula 2-5] was 52 GM at 750 nm.

In HEPES/EtOH (1/1), the action cross section ($\phi\delta$) of the compound of [Chemical Formula 2-6] was increased 12-fold and that of the compound of [Chemical Formula 2-5] was increased about 2-fold (Table 1). The larger action cross section ($\phi\delta$) measured in HEPES/EtOH (1/1) may have resulted from the larger fluorescence quantum yield ($\phi$) in a more hydrophobic solvent (Table 1).

Figure 1:
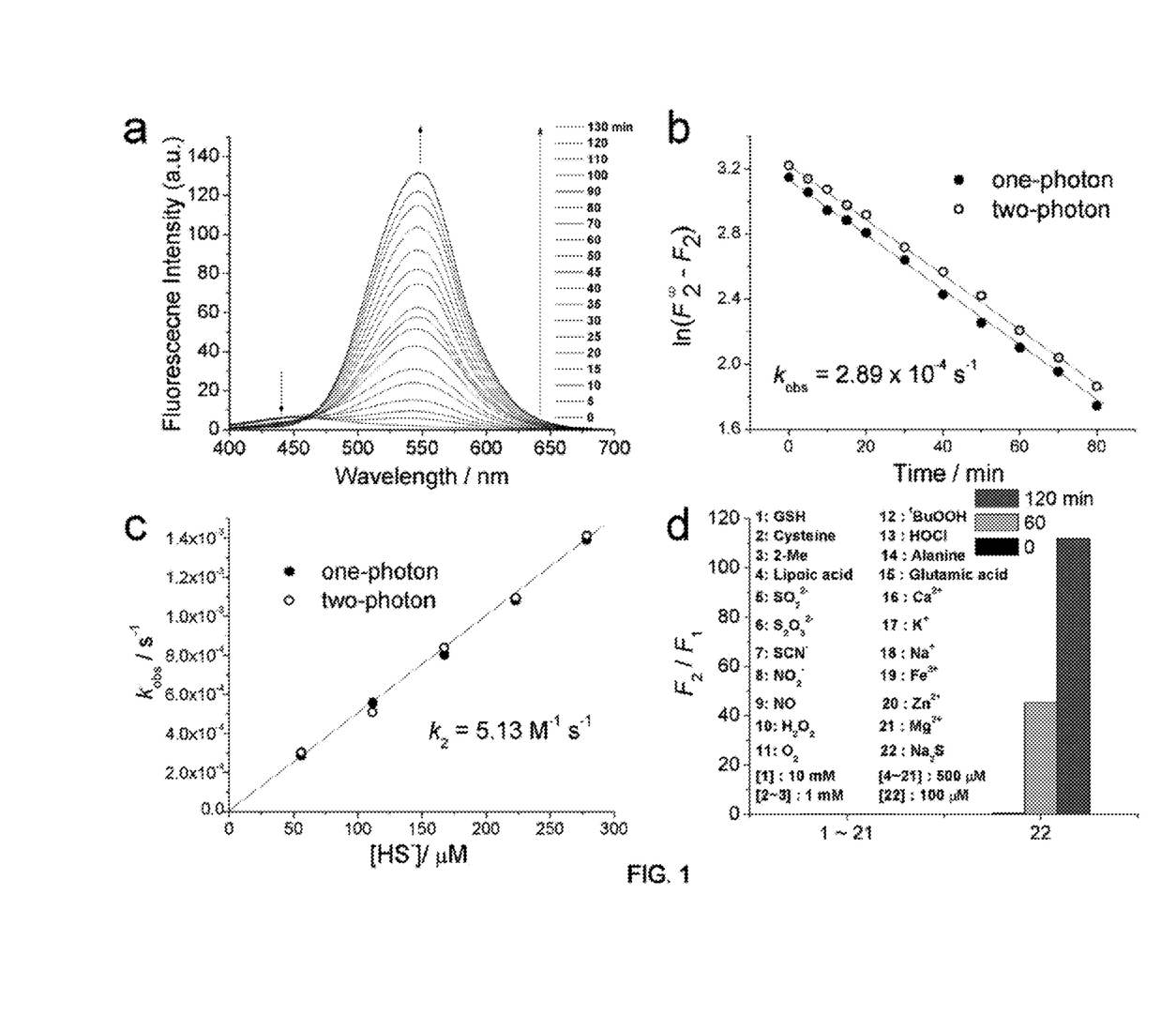
FIG. 1a shows a result of one-photon fluorescence reaction between a compound of [Chemical Formula 2-6] (5 μM) and $Na_2S$ (100 μM) with time (0-120 min).
FIG. 1b shows plots of $\ln(F^\infty_2-F_2)$ against time t for a reaction between a compound of [Chemical Formula 2-6] (5 μM) and $Na_2S$ (100 μM) monitored by one-photon and two-photon processes. $F^\infty_2$ and $F_2$ respectively are fluorescence intensities measured after 10 half-lives and at a given time.
FIG. 1c shows a plot of $k_{obs}$ against $[HS^-]$.
FIG. 1d shows fluorescence intensities of a compound of [Chemical Formula 2-6] (5 μM) for 100 μM $Na_2S$, other active sulfides, nitrogen compounds, oxygen species, amino acids and metal ions. The ratio of fluorescence intensities ($F_2/F_1$) measured at a short wavelength ($F_1$) and a long wavelength ($F_2$) at 0, 60 and 120 min is shown. All the data were obtained at 37° C. in HEPES buffer. Excitation wavelengths for one-photon and two-photon processes were 370 nm (short wavelength) and 750 nm (long wavelength), respectively.

$k_{obs}$ and $k_2$ values measured for the one-photon and two-photon process were almost identical (FIGS. 1b and 1c). This result means that the two-photon (TP) excited fluorescence intensity of cells and tissues labeled with the compound of [Chemical Formula 2-6] can be monitored.

In addition, the usefulness of the compound of [Chemical Formula 2-6] in detection of $H_2S$ in living cells was tested.

Using 750 nm TP excitation in scanning lambda mode, HeLa cells treated with 100 mM $Na_2S$ and labeled with the compound of [Chemical Formula 2-6] exhibited maximum emission and fluorescence intensity ratio similar to those of the compound of [Chemical Formula 2-6] and the compound of [Chemical Formula 2-5] measured in HEPES/EtOH (1/1) and showed broad spectra that could be dissected into two Gaussian functions (FIG. 2b). This confirms again that HEPES/EtOH (1/1) is a good model of the cellular environment and HS⁻ can be detected by TPM using the compound of [Chemical Formula 2-6].

The two-photon excited fluorescence (TPEF) intensities of the compound of [Chemical Formula 2-6] and the compound of [Chemical Formula 2-5] could be detected with minimum interference at 390-450 nm and 525-650 nm, respectively.

Also, the detection limit of TPM for HS⁻ using the compound of [Chemical Formula 2-6] in vivo was found to be 0.086 μM.

Measurement of Two-Photon Cross Section

Two-photon cross section ($\delta$) was determined using a femtosecond (fs) fluorescence measurement technique.

The compound of [Chemical Formula 2-5] and the compound of [Chemical Formula 2-6] were dissolved in 20 mM HEPES buffer (pH 7.2) and $3.0\times10^{-6}$ M HEPES/EtOH (1/1) and then two-photon induced fluorescence intensity was measured at 740-940 nm using rhodamine 6G as a reference, whose two-photon property has been well characterized. The two-photon fluorescence intensities of the reference and the compound of [Chemical Formula 2-6] and the compound of [Chemical Formula 2-5] were determined.

The two-photon cross section was calculated from $\delta=\delta_r (S_s\phi_r\phi_r c_r)/(S_r\phi_s\phi_s c_s)$. In the equation, the subscripts s and r stand for the sample, i.e., the compound of [Chemical Formula 2-6] and the compound of [Chemical Formula 2-6], and the reference, respectively. S denotes the intensity of the signal collected using a CCD detector, $\phi$ is the fluorescence quantum yield (measured using coumarin 307 and rhodamine B according to the literature), $\phi$ is the overall fluorescence collection efficiency, and c is the number density of molecules in solution. $\delta_r$ is the two-photon cross section of the reference molecule.

Test Example 3

Mechanism of Reaction Between Compound of [Chemical Formula 2-6] and Sulfide

Figure 10:
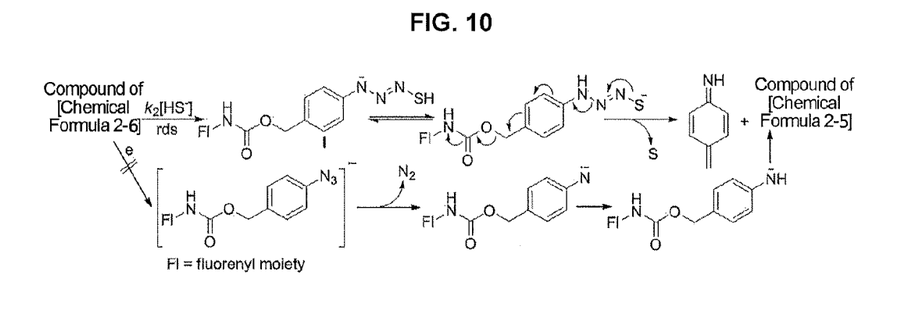
FIG. 10 shows a scheme used in the preparation of a reaction between compound [Chemical 2-6] and a sulfide.

The reaction between the compound of [Chemical Formula 2-6] (5 mM) and NaHS (300 μM) in HEPES buffer and HEPES/EtOH (1/1), as shown in FIG. 10, was performed at 37° C. for 2 hours and monitored by LC-MS analysis. As a result, the compound of [Chemical Formula 2-5] was obtained as the only major product. For example, the compound of [Chemical Formula 2-6] was synthesized from the reaction of the compound of [Chemical Formula 2-5] and HS⁻. Also, precipitation of sulfur or sulfide was reported in the reaction between phenyl azide and $Na_2S$.

When 100 μM $Na_2S$ was added to the compound of [Chemical Formula 2-6] in HEPES buffer at 37° C., the fluorescence intensity of the compound of [Chemical Formula 2-6] was slightly decreased at 390-450 nm and, as a result, the fluorescence intensity of the compound of [Chemical Formula 2-5] was slightly increased at 525-650 nm (FIG. 1a). This followed pseudo first-order kinetics with $k_{obs}=2.89\times 10^{-4}$ s⁻¹ (FIG. 1b).

Since the $pK_1$ and $pK_2$ values of $H_2S$ are 6.96 and 12.90, respectively, $H_2S$ and HS⁻ are the predominant sulfide species in aqueous solution regardless of whether $Na_2S$, NaHS or $H_2S$ is used as the sulfide donor. Also, since HS⁻ is a much better nucleophile than $H_2S$, HS⁻ should be the major reactive species under the reaction condition.

The plot of $k_{obs}$ vs. [HS⁻] was a straight line passing the origin (FIG. 1c), indicating that the reaction was second-order overall, first-order with respect to HS⁻ and first-order with respect to the compound of [Chemical Formula 2-6]. The $k_2$ value calculated from the slope of the plot was 5.13 M⁻¹s⁻¹ (measured in HEPES buffer).

A similar result was observed in HEPES/EtOH (1/1) (Table 1), which is a good model for the intracellular environment, except that the fluorescence intensity at 390-450 nm decreased more sharply because of the larger fluorescence quantum yield of the compound of [Chemical Formula 2-6] in the solvent. The $k_2$ value in HEPES/EtOH (1/1, pH=7.2) calculated using $pK_a$ ($H_2S$)=7.10 was 5.17 M⁻¹s⁻¹. The $k_2$ value was very similar to that measured in HEPES buffer.

Moreover, the $k_{obs}$ value was not influenced by the addition of p-dinitrobenzene, a strong electron acceptor, negating the possibility of the electron transfer mechanism. These results suggest that the reaction proceeds by the rate-limiting attack of HS⁻ followed by the decomposition of the resulting adduct (I) as depicted in [Scheme 2].

$pK_a$ Value of $H_2S$ in HEPES/EtOH (1/1, pH 7.2) at 37.0° C.

The $pK_a$ value of $H_2S$ in HEPES/EtOH (1/1, pH 7.2) was estimated by using the following equations.

$$HS^- + H_2O \rightleftharpoons H_2S + HO^- \quad K_1 = [H_2S][HO^-]/[HS^-] \tag{1}$$

$$H_2O \rightleftharpoons H^+ + HO^- \quad K_w = [H^+][HO^-] \tag{2}$$

$$H_2S \rightleftharpoons H^+ + HS^- \quad K_a = [H^+][HS^-]/[H_2S] = K_w/K_1 \tag{3}$$

First, the pH of the solution containing 10.0 mM NaSH was measured in $H_2O$/EtOH (1/1) at 37.0° C. using a pH meter. The pH was 9.00.

The $K_1$ value was calculated from the equation (1) using $[HS^-]_o=10.0$ mM and pH=9.00. The value was $1.00\times10^{-8}$ M.

The $pK_a$ value of $H_2S$ in HEPES/EtOH (1/1, pH 7.2) was then calculated from the equation (3) using $K_1=1.00\times10^{-8}$ M and $pK_w=15.10$ reported in $H_2O$/EtOH (1/1). The calculated $pK_a$ value was 7.10.

Test Example 4

Measurement of Selectivity of Compound of [Chemical Formula 2-6] for Sulfide

To test whether the compound of [Chemical Formula 2-6] can selectively detect $HS^-$ over other biologically relevant species, the ratiometric response of the compound of [Chemical Formula 2-6] was determined in the presence of various analytes.

The relative fluorescence intensity ratio ($F_2/F_1$) measured at the short wavelength ($F_1$, ~350-550 nm) and long wavelength ($F_2$, 560-780 nm) regions of the compound of [Chemical Formula 2-6] in the presence of 100 mM $Na_2S$ (55.7 mM $HS^-$) in HEPES buffer showed a 110-fold increase, higher than that of the compound of [Chemical Formula 2-5] (FIG. 1d). This result confirms that the compound of [Chemical Formula 2-6] can serve as a ratiometric two-photon fluorescent dye for $HS^-$.

In contrast, the compound of [Chemical Formula 2-6] exhibited no reactivity toward 10 mM glutathione (GSH, 100 times larger amount than $H_2S$ tested), 1 mM cysteine (Cys) and 1 mM 2-mercaptoethanol (2-ME), as well as other biologically relevant reactive sulfur species (RSS; lipoic acid, $SO_3^{2-}$, $S_2O_3^{2-}$, $SCN^-$), reactive nitrogen species (RNS; $NO_2^-$, NO), reactive oxygen species (ROS; $H_2O_2$, $O_2^-$, t-BuOOH, HOCl), amino acids without thiol groups (Ala, Glu) and metal ions ($Ca^{2+}$, $K^+$, $Na^+$, $Fe^{3+}$, $Zn^{2+}$, $Mg^{2+}$) (FIG. 1d).

As can be seen from FIG. 1d, the compound showed small reactivity toward commercially available GSH, as reported for other azide-containing probes, but no reactivity toward purified GSH.

The negligible reactivity for GSH, Cys and 2-ME, which cannot form the intermediate (I) with ionizable HS bond, provided additional support for the mechanism shown in [Scheme 6].

Moreover, the compound of [Chemical Formula 2-6] and the compound of [Chemical Formula 2-5] were pH-insensitive in the biologically relevant pH range. These results suggest that the compound of [Chemical Formula 2-6] can detect intracellular $HS^-$ with minimum interference from other biologically relevant analytes and pH values.

Test Example 5

Quantitative Estimation of Total Sulfide Concentration in HeLa Cells

To quantitatively estimate the total sulfide concentration in living cells, the TPEF intensity of HeLa cells labeled with the compound of [Chemical Formula 2-6] was monitored in the absence and presence of $Na_2S$, cysteine (Cys) and glutathione (GSH) with 20-30 minute intervals. The TPEF intensity of the HeLa cells labeled with the compound of [Chemical Formula 2-6] remained nearly constant during the measurement, i.e., $k_{obs}=(0.0\pm0.1)$ $s^{-1}$. This result indicates that the intracellular total sulfide concentration is nearly zero.

Figure 3:
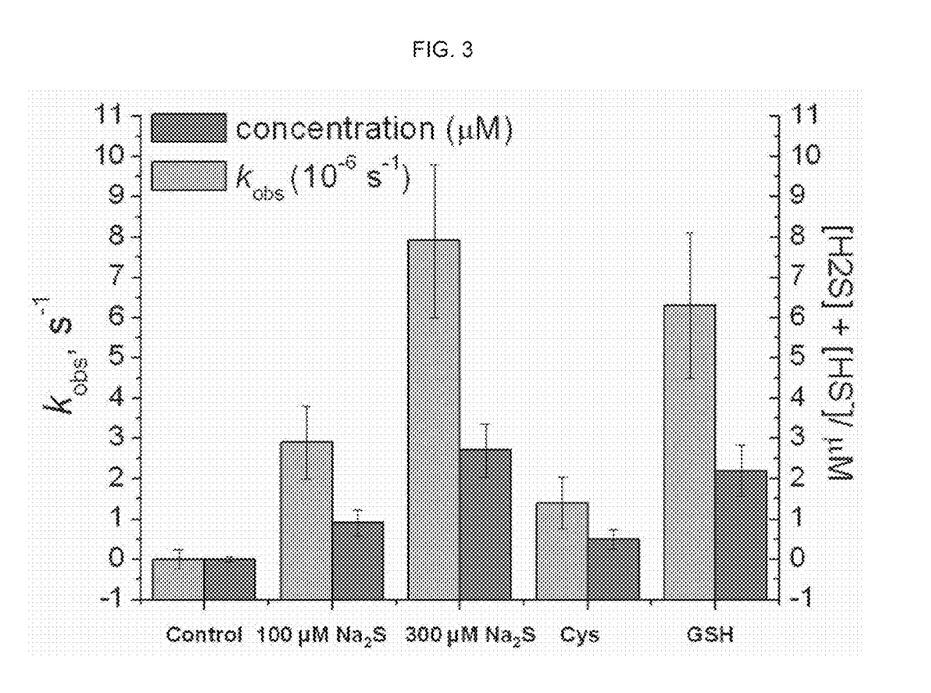
FIG. 3 shows average $k_{obs}$ and sulfide concentration in HeLa cells before and after treatment with 100-300 μM $Na_2S$, cysteine and glutathione. The error bars indicate 95% confidence intervals based on $k_{obs}$=30.

When the cells were pretreated with 100 μM $Na_2S$ and 300 μM $Na_2S$ before labeling with the compound of [Chemical Formula 2-6], the TPEF intensity increased slowly with $k_{obs}=(2.6\pm0.9)\times10^{-6}$ and $(7.9\pm1.9)\times10^{-6}$ $s^{-1}$, respectively (FIG. 3).

Since $H_2S$ and $HS^-$ are in equilibrium and $[H_2S]/[HS^-]=[H^+]/K_a=0.794$ in HEPES/EtOH (1/1, pH=7.2), it seems appropriate to present the total sulfide concentration ($[H_2S]+[HS^-]$).

The total sulfide concentrations calculated using $k_{obs}=k_2[HS^-]$, $k_2=5.17$ $M^{-1}s^{-1}$ and $[H_2S]/[HS^-]=0.794$ were $0.90\pm0.32$ μM and $2.7\pm0.7$ μM in the cells pretreated with 100 μM $Na_2S$ and 300 μM $Na_2S$, respectively. This result indicates that either small fraction of the $H_2S$ penetrates the cell membrane or excess sulfide is quickly removed from the cellular environment by various degradative pathways. This result is in contrast to the generally accepted view that $H_2S$ can freely penetrate the cell membrane because it is lipophilic.

When the cells were treated with 500 μM Cys or GSH, the $k_{obs}$ value increased from 0.0 to $(1.4\pm0.7)\times10^{-6}$ $s^{-1}$ and $(6.3\pm1.8)\times10^{-6}$ $s^{-1}$, respectively, which corresponds to an increase in the total sulfide concentration from $0.0\pm0.1$ μM to $0.50\pm0.23$ μM and $2.2\pm0.6$ μM, respectively (FIG. 3). These additives seem to stimulate the cells to produce extra sulfides, but the effect appears to be modest.

Further, the compound of [Chemical Formula 2-6] showed negligible toxicity as measured using the CCK-8 kit and high photostability as indicated by the negligible decay in the TPEF intensity at a given spot on the HeLa cells labeled with the compound of [Chemical Formula 2-6] after continuous radiation of fs-pulses for 60 minutes. These findings confirm that the compound of [Chemical Formula 2-6] can measure the total sulfide concentration in living cells by the kinetic method with minimum interference from cytotoxicity and photostability.

Kinetic Studies in Solution

Reactions of the compound of [Chemical Formula 2-6] (5 μM) with $Na_2S$ (100-500 μM) in HEPES buffer or HEPES/EtOH (1/1, pH 7.2) were followed by monitoring of the increase in the fluorescence of the compound of [Chemical Formula 2-5] at 525-650 nm using a luminescence spectrometer.

The kinetic studies in a TP mode were conducted by the same procedure described above except that the TPEF was collected upon excitation at 750 nm.

In all cases, the plots of $-\ln(F^\infty_2-F_2)$ vs. t were linear with good correlations. The $k_{obs}$ values were obtained from the slopes of the plots and the $K_2$ values were obtained from the slopes of the plots of $k_{obs}$ vs. $[HS^-]$. $[HS^-]$ was calculated by assuming that all of the $Na_2S$ was converted to $HS^-$ and $H_2S$, that is, $[Na_2S]=[H_2S]+[HS^-]$, and using the relationship $[H_2S]/[HS^-]=[H^+]/K_a=0.794$ in HEPES/EtOH (1/1, pH=7.2).

Test Example 6

Figure 4:
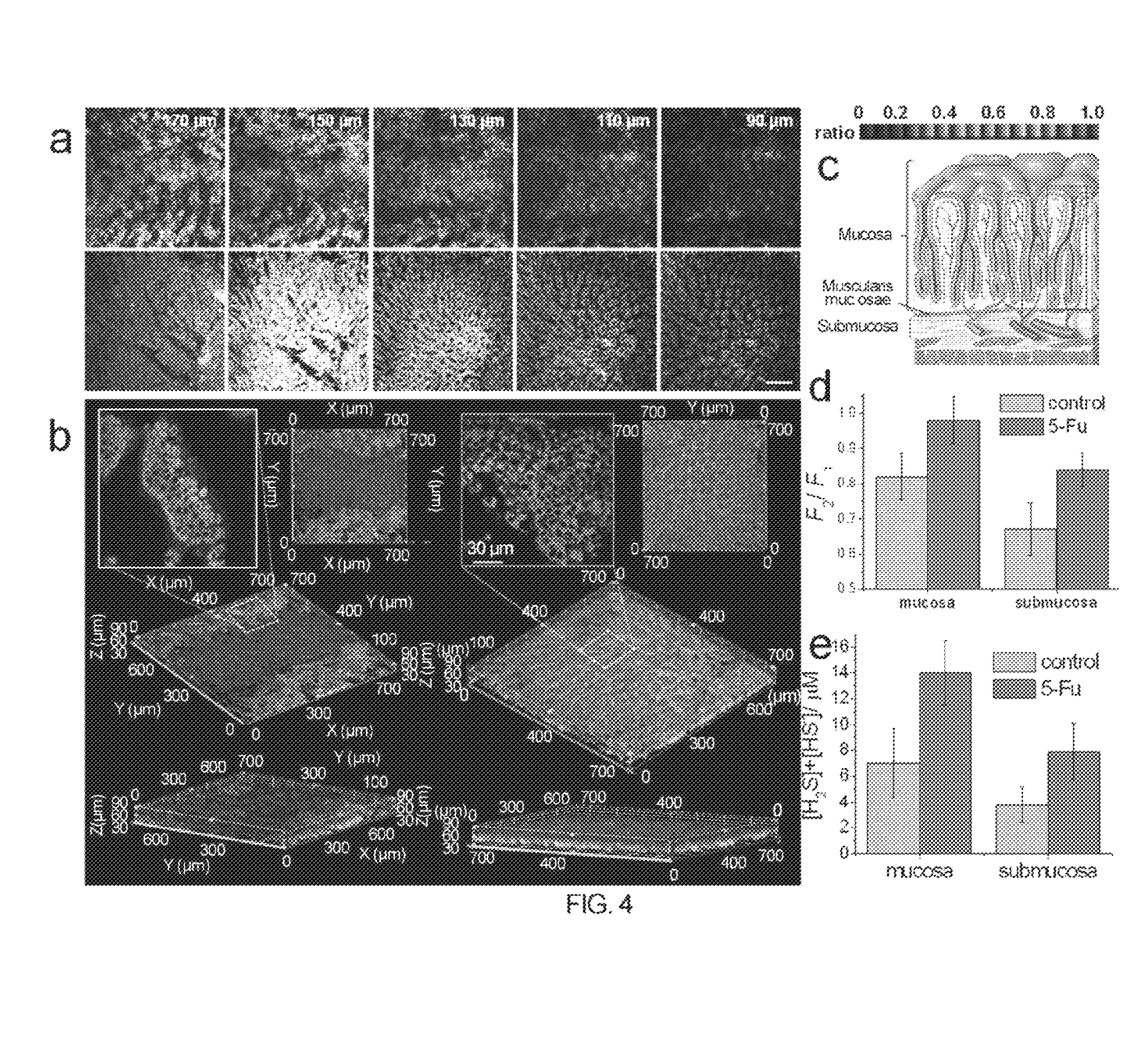
FIG. 4a shows ratiometric TPM images (20×) of rat colon tissues labeled with a compound of [Chemical Formula 2-6] (20 μM). The TPM images show colon tissues before (top) and after (bottom) treatment with 5-fluorouracil for 8 hours at a depth of about 90-170 μm. Scale bar: 150 μm.
FIG. 4b shows 3-dimensional images (20×) of colon tissue constructed from 150 TPM images before (left) and after (right) treatment with 5-fluorouracil for 8 hours at a depth of about 90-170 µm (top, tilted and side views). The white boxes are magnified images (100×) of the selected area.
FIG. 4c shows mucosa, muscularis mucosae and submucosa tissue layers.
FIG. 4d shows $F_2/F_1$ ratios measured after incubating mucosa and submucosa tissues with a compound of [Chemical Formula 2-6] (20 µM) for 2 hours before and after treatment with 5-fluorouracil. The error bars indicate 95% confidence intervals based on $F_2/F_1$ ratio=105 and 45, respectively, for the mucosa and submucosa tissues.
FIG. 4e shows total sulfide concentrations in mucosa and submucosa tissues measured before and after treatment with 5-fluorouracil. The error bars indicate 95% confidence intervals based on $F_2/F_1$ ratio=105 and 45 and $k_{obs}$=112 and 48, respectively, for the mucosa and submucosa tissues.

The utility of the compound of [Chemical Formula 2-6] was investigated in living tissues from a 5-week-old rat colon. The inventors were particularly interested in the mucosa, muscularis mucosae and submucosa because they are invaded in the early stage of tumor (FIG. 4c). Since it takes a long time to stain the tissues during which they may be deformed, excess amount (20 μM) of the compound of [Chemical Formula 2-6] was used to facilitate staining.

Because the structure of the colon tissue is heterogeneous, TPEF intensities were acquired from 150 sections along the z-direction at a depth of about 90-170 μm using two detection windows (1 and 2) to visualize the overall sulfide distribution.

The two-photon microscopy (TPM) ratiometric images constructed from $F_2/F_1$ revealed that the glands were clearly visible up to a depth of 146 μm and began to disappear at higher depths (FIG. 4a). Therefore, the sections were divided into two regions and they were assigned as mucosa (90-150 μm) and submucosa including the muscularis mucosae (151-170 μm).

The two-photon microscopy (TPM) ratiometric images revealed that the basal sulfide level is higher in mucosa than in submucosa with the average emission ratios of 0.82±0.07 and 0.67±0.07, respectively (FIG. 4d).

The larger $F_2/F_1$ ratio measured in the mucosa is as expected because the mucosa is lined with columnar epithelial cells, while the submucosa is composed of connective tissues.

When the rats were treated with 5-fluorouracil (5-FU), the emission ratio of the tissue slice increased slightly to 0.98±0.07 in the mucosal layer and to 0.84±0.05 in the submucosa. The increase in the $F_2/F_1$ ratio after treatment with 5-FU is consistent with the proposal that it may elevate the sulfide level by inducing mucosal inflammation. Moreover, the $F_2/F_1$ ratio is much smaller than $F_2/F_1$=110 measured in HEPES buffer after deazidation. This result is consistent with the low sulfide concentration estimated by the kinetic method. However, this ratio cannot be converted to the total sulfide concentration. That is, the ratiometric measurements can provide qualitative information, not quantitative data.

To quantitatively estimate the total sulfide concentration, kinetic experiments were performed in the colon tissue labeled with the compound of [Chemical Formula 2-6].

The $k_{obs}$ values determined in the mucosa and the submucosa were $(2.0\pm0.8)\times10^{-5}$ s$^{-1}$ and $(1.1\pm0.5)\times10^{-5}$ s$^{-1}$, respectively.

Upon treating with 5-FU, the $k_{obs}$ values doubled to $(4.0\pm0.7)\times10^{-5}$ s$^{-1}$ in the mucosa and to $(2.3\pm0.6)\times10^{-5}$ s$^{-1}$ in the submucosa.

The total sulfide concentrations in the mucosa and submucosa tissues doubled upon 5-FU treatment, from 7.0±2.7 μM and 3.8±1.4 μM before treatment, to 14±3 μM and 7.9±2.2 μM after 5-FU treatment, respectively (FIG. 4e). The higher sulfide concentration in the mucosa than in the submucosa as well as the increased total sulfide concentration after the treatment with 5-FU is in good agreement with the larger $F_2/F_1$ ratio measured under the same condition. However, these values are much smaller than that of 50-160 μM measured in the rat brain tissue.

These findings confirm that the compound of [Chemical Formula 2-6] can quantitatively estimate the total sulfide concentration in different layers of rat colon tissue within 20-40% accuracy by the kinetic method. However, the large error involved in the measurement is primarily due to the heterogeneous nature of the tissue slices taken from different rats, not due to the kinetic model presented here.

Cell Culture

HeLa human cervical carcinoma cells were acquired from the ATCC (Manassas, Va., USA). The cells were cultured in DMEM (WelGene, Inc., Seoul, Korea) supplemented with heat-inactivated 10% FBS (WelGene), penicillin (100 units/mL) and streptomycin (100 mg/mL).

All the cell lines were maintained in a humidified atmosphere of 5% $CO_2$ and 95% air at 37° C.

Two days before imaging, the cells were moved onto glass-bottomed dishes (MatTek).

For labeling, the growth medium was removed and replaced with DMEM without FBS. The cells were incubated with the compound of [Chemical Formula 2-6] (2 mM) for 30 minutes, washed 3 times with FBS-free DMEM and imaged.

Cell Viability

To confirm that the compound does not affect the viability of HeLa cells under the incubation condition, the CCK-8 kit (Cell Counting Kit-8, Dojindo, Japan) was used according to the manufacturer's protocol.

Two-Photon Microscopy Imaging

TPM images of the cells and tissues labeled with the compound of [Chemical Formula 2-6] were obtained using spectral confocal and multiphoton microscopes with ×100 (NA=1.30 OIL) and ×40 (NA=0.75 DRY) objective lenses, respectively.

The TPM images were obtained with the DM IRE2 microscope (Leica) by exciting the probes with a mode-locked titanium-sapphire laser source (Coherent Chameleon, 90 MHz, 200 fs) set at a wavelength of 750 nm and an output power of 1380 mW, which corresponded to an average power of approximately 2 mW in the focal plane.

To obtain ratiometric images, internal PMTs were used to collect signals at 390-450 nm and 520-650 nm regions in 8-bit unsigned 512×512 pixels at a scan rate of 400 Hz.

Preparation, Staining and Ratiometric Imaging of Rat Colon Slices

The protocol followed the Korean Code of Practice for the Care and Use of Animals and was approved by the Animal Ethics Committee of the Korea University Anam Hospital (Seoul, Korea).

Male Sprague-Dawley rats (235-265 g) were divided into two groups (5-FU and control groups). In the 5-FU group, 150 mg/kg of 5-FU (SoloPak Laboratories, Franklin Park, Ill.) were intraperitoneally injected into the rats. The rats of the control group were injected with saline. Each group consisted of 4 rats.

All the rats were injected between 9 pm and 12 midnight, were allowed free access to food and water and were housed in the same room with 8-hour cycles.

8 hours after the intraperitoneal injection, all the rats were sacrificed. Laparotomy was performed after anesthetizing the rats.

Slices were prepared from the colon of the rats. The colon slices were cut into 2-cm long segments, opened by longitudinal incision and then treated with Dulbecco's phosphate-buffered saline (D-PBS; 200 mM KCl, 200 mM $KH_2PO_4$, 8 M NaCl, 2.16 M $Na_2HPO_4$—$H_2O$).

The colon slices were incubated with the compound of [Chemical Formula 2-6] (20 μM) in D-PBS bubbled with 95% $O_2$ and 5% $CO_2$ at 37° C. The colon slices were then moved to glass-bottomed dishes, washed 3 times with D-PBS and observed under a confocal multiphoton microscope.

TPEF intensities were collected using detection windows of 390-450 nm and 520-650 nm, with 110 sections at a depth of 90-150 μm (mucosa) and 40 sections at a depth of 151-170 μm (submucosa).

Then ratiometric images were constructed from the TPEF intensities collected using the two detection window. The $F_2/F_1$ ratio was expressed as mean±SD and p was set to be smaller than 0.05.

Kinetic Measurement in Cells and Tissue Slices

Kinetic experiments in HeLa cells were conducted in the same manner except that TPEF intensities from HeLa cells labeled with the compound of [Chemical Formula 2-6] upon excitation at 750 nm were monitored with 20-30 minute intervals.

The average TPEF intensities at given time and the $S_{B2}/S_{A1}$ ratio was obtained by dividing the TPEF intensity of [Chemical Formula 2-6] at 390-450 nm by that of [Chemical Formula 2-5] at 525-650 nm in the HeLa cells (FIG. 1b) were used in the $k_{obs}$ calculation.

The $k_{obs}$ value was measured at 10 regions of interest (ROIs) from three independent cell lines.

To evaluate the effect of $Na_2S$, cysteine and GSH, HeLa cells were incubated with the compound of [Chemical Formula 2-6] (2 μM) and then treated with $Na_2S$ (100, 300 μM), cysteine (500 μM) and GSH (500 μM) for 30 minutes. The cells were then washed 3 times with FBS-free DMEM and subjected to kinetic measurement.

Kinetic experiments in rat colon tissue were performed using four colon slices obtained from four rats. Two sets of experiments were performed for each slice. In each set, TPEF intensities from 8 ROI's/section were collected at depths of 90-150 μm (mucosa) and 151-170 μm (submucosa) in the colon tissue labeled with the compound of [Chemical Formula 2-6] and averaged.

The rate constant ($k_{obs}$) was measured from 7 and 3 sections of the mucosa and submucosa tissues, respectively, in order to obtain 112 $k_{obs}$ and 48 $k_{obs}$ values, respectively. The rate constant ($k_{obs}$) was expressed as mean±SD and p was set to be smaller than 0.05.

What is claimed is:

1. A two-photon fluorescent dye for imaging total sulfide ($[H_2S]+[HS^-]$) in vivo, comprising a compound of (Chemical Formula 2-6):

(Chemical Formula 2-6)

2. The two-photon fluorescent dye for imaging total sulfide in vivo according to claim 1, wherein the two-photon fluorescent dye is excited by a femtosecond pulse with a wavelength of 700-800 nm.

3. The two-photon fluorescent dye for imaging total sulfide in vivo according to claim 1, wherein the two-photon fluorescent dye detects hydrosulfide ion ($HS^-$) at a penetration depth of 100 μm or greater in vivo.

4. The two-photon fluorescent dye for imaging total sulfide in vivo according to claim 1, wherein two-photon fluorescent dye images total sulfide at a penetration depth of 100 μm or greater in vivo.

5. The two-photon fluorescent dye for imaging total sulfide in vivo according to claim 1, wherein the two-photon fluorescent dye has a two-photon action cross section ($\Phi\delta_{max}$) of 10-30 GM at a wavelength of 740 nm.

6. The two-photon fluorescent dye for imaging total sulfide in vivo according to claim 1, wherein the two-photon fluorescent dye has a ratio of fluorescence intensities ($F_2/F_1$) measured at a short wavelength ($F_1$, ~350-550 nm) and a long wavelength ($F_2$, 560-780 nm) of 0.5-1.0.

7. A method for quantitatively estimating total sulfide concentration in vivo using a reaction rate constant ($k_{obs}$), $k_2$ and a concentration ratio $[H_2S]/[HS^-]$ from a reaction of a compound of (Chemical Formula 2-6) with hydrosulfide ion ($HS^-$) in vivo:

(Chemical Formula 2-6)

and $k_2$ is obtained as a slope of a curve of the reaction rate constant ($k_{obs}$) vs. $[HS^-]$.

* * * * *